United States Patent
Hart

(10) Patent No.: US 8,523,943 B2
(45) Date of Patent: Sep. 3, 2013

(54) METHOD AND DEVICE FOR THE FIXATION OF A TENDON GRAFT

(75) Inventor: Rickey Hart, Marco Island, FL (US)

(73) Assignee: Karl Storz GmbH & Co. KG (DE)

(*) Notice: Subject to any disclaimer, the term of this patent is extended or adjusted under 35 U.S.C. 154(b) by 425 days.

(21) Appl. No.: 12/610,904

(22) Filed: Nov. 2, 2009

(65) Prior Publication Data

US 2011/0106112 A1    May 5, 2011

(51) Int. Cl.
*A61F 2/08*    (2006.01)
*A61B 17/08*    (2006.01)

(52) U.S. Cl.
USPC ............ 623/13.14; 623/13.11; 623/13.12; 623/13.13; 606/151

(58) Field of Classification Search
USPC ............ 623/13.11–13.18; 606/62, 68, 72, 606/73, 151, 157, 232
See application file for complete search history.

(56) References Cited

U.S. PATENT DOCUMENTS

| | | | |
|---|---|---|---|
| 5,002,574 A * | 3/1991 | May et al. | 623/13.13 |
| 5,306,301 A | 4/1994 | Graf et al. | |
| 6,086,591 A | 7/2000 | Bojarski | |
| 6,283,996 B1 | 9/2001 | Chervitz et al. | |
| 6,440,134 B1 | 8/2002 | Zaccherotti et al. | |
| 6,562,071 B2 | 5/2003 | Järvinen | |
| 6,685,706 B2 | 2/2004 | Padget et al. | |
| 2004/0073219 A1 | 4/2004 | Skiba et al. | |
| 2004/0073306 A1 | 4/2004 | Eichhorn et al. | |
| 2006/0189991 A1 | 8/2006 | Bickley | |

FOREIGN PATENT DOCUMENTS

| | | |
|---|---|---|
| GB | 2370227 A | 6/2002 |
| WO | 9811839 A1 | 3/1998 |
| WO | 2006062419 A1 | 6/2006 |

OTHER PUBLICATIONS

European Search Report; Application No. EP 10 18 9671; Mar. 2, 2011; 7 pages.

* cited by examiner

*Primary Examiner* — David Isabella
*Assistant Examiner* — Yashita Sharma
(74) *Attorney, Agent, or Firm* — St. Onge Steward Johnston & Reens LLC

(57) ABSTRACT

A fixation device for securing a transplant in a bone tunnel, having a strap with a plurality of protrusions disposed along its length, a fastening member with an aperture therein for passing the strap, and a connection element disposed at a distal end of the strap for engaging a transplant is provided. The fixation device is configured such that, when the distal side of the fastening member lies substantially flush against an outer surface of the bone, a longitudinal axis of the aperture is substantially parallel to a longitudinal axis of the bone tunnel. A method for securing a transplant in a bone tunnel using the aforementioned fixation device is also provided.

11 Claims, 8 Drawing Sheets

METHOD AND DEVICE FOR THE FIXATION OF A TENDON GRAFT

FIELD OF THE INVENTION

The invention relates to a device and method for use in tissue repair or replacement, more specifically, to fixating a graft relative to a bone.

BACKGROUND OF THE INVENTION

Damage to ligaments, such as anterior cruciate ligaments (ACL) and the posterior cruciate ligaments (PCL), cartilage, and tendons has become a relatively common occurrence and often requires surgical repair. Often, the ACL or the PCL is ruptured or torn as a result of physical activity and, consequently, various surgical procedures have been developed for replacing or reconstructing these ligaments.

The knee joint is often repaired by substituting a harvested or synthetic replacement ligament for the damaged one. Commonly, a substitute ligament or graft is inserted into tunnels reamed in the femur and tibia bones. Once anchored in place, the graft ligament is able to cooperate with the surrounding bone and tissues and thereby perform the functions of the damaged ACL or PCL.

Several methods and devices have been developed for fixating a graft or ligament or tendon into a bone tunnel. However, these known devices and techniques often require complicated implantation procedures or involve coordination of several discrete pieces. For example, U.S. Pat. No. 5,306,301 teaches a complicated draw string arrangement for securing a graft in a button-like footing. U.S. Pat. No. 6,562,071 features an anchoring member that requires a separate clamp member in order to secure it into a bone tunnel. Moreover, in ACL repair surgery, it is not typical that the bone tunnel be drilled perpendicular to the surface of the bone. Therefore, other known devices suffer from the problem that the anchoring device does not lie flush with the outer surface of the bone, creating a protuberance than can be problematic for the patient. For example, while the Figures in U.S. Pat. No. 6,283,996 illustrate the footing lying flush against the surface of the bone, this would not be the case in an actual surgical setting.

It is therefore desirable to have a fixation device for easily and securely fixating a tendon or ligament graft within a femoral tunnel. In addition, it is desirable to have a fixation device that lies flat against the outer surface of the bone so as to have a low profile.

SUMMARY OF THE INVENTION

Accordingly, it is an object of the present invention to provide a method and device for easily and securely fixating a graft within a bone tunnel that is drilled at some non-perpendicular angle with respect to the outer surface of the bone, wherein the device lies flat against the surface of the bone.

These and other objectives are achieved by providing a fixation device for securing a transplant in a bone tunnel, comprising a strap having a plurality of protrusions disposed along its length, a fastening member having an aperture therein for passing the strap, and a connection element disposed at a distal end of said strap for engaging a transplant. The fastening member further comprises a distal side, a longitudinal axis of the aperture being substantially parallel to a longitudinal axis of the bone tunnel when the fastening member distal side lies substantially flush against an outer surface of the bone. In another embodiment, the longitudinal axis of the aperture is coaxial with the longitudinal axis of said bone tunnel. More specifically, the aperture may traverse the fastening member at a 45 degree angle.

In a further embodiment, the connection element further comprises a shoulder for engaging a notch within the bone tunnel. The notch may be defined by the intersection of a first tunnel section in the bone disposed proximally of a second tunnel section in a bone, the first and second tunnel sections being coaxial, the first tunnel section having a radius smaller than a radius of the second tunnel section.

In still a further embodiment, the fastening member comprises a self-locking element for engaging at least one of the protrusions and preventing the strap from moving in a distal direction when a tensile force is applied thereto. The plurality of protrusions comprise a plurality of teeth and the self-locking element may comprise a pawl shaped to engage at least one of said plurality of teeth. The teeth may comprise a proximal side and a distal side, the proximal side of each of the teeth sloping downwards towards a proximal end of the strap.

In some embodiments, the connection element may comprise an eyelet for receiving a portion of said transplant therethrough. In other embodiments, the connection element may comprise a wedge for pressing a transplant against an inner surface of said bone tunnel. In still further embodiments, the connection element may comprise at least one prong for engaging a hole in a bone block of a transplant.

A method for securing a transplant in a bone tunnel, comprising the steps of: forming a tunnel in a bone; providing a fixation device for securing a transplant in said tunnel, having a strap with a plurality of protrusions disposed along its length, a fastening member with an aperture therein for passing the strap, and a connection element disposed at a distal end of said strap for engaging a transplant, said fastening member further comprising a distal side, a longitudinal axis of said aperture being substantially parallel to a longitudinal axis of said bone tunnel when said fastening member distal side lies substantially flush against an outer surface of the bone; engaging a transplant on said connection element; passing a proximal end of said strap through said tunnel; passing a proximal end of said strap through said aperture; and moving said fastening member in a distal direction down said strap until an undersurface of said fastening member engages the bone is also provided.

In a further embodiment, the step of forming a tunnel in a bone further comprises the steps of forming a first tunnel section in a bone and forming a second tunnel section in a bone proximally of said first tunnel section, the first and second tunnel sections being coaxial, the first tunnel section having a radius smaller than a radius of the second tunnel section. The intersection of the first and second tunnel sections define a notch in the bone tunnel. In some embodiments, the connection element further comprises a shoulder for engaging the notch. In still a further embodiment, the method further comprises the step of removing a portion of the strap extending distally of the fastening member.

These and other objectives may also be achieved by providing a fixation device for securing a transplant in a bone tunnel, comprising: a strap having a plurality of protrusions disposed along its length; a fastening member having an aperture therein for passing the strap; and a connection element disposed at a distal end of said strap for engaging a transplant. The aperture may traverse the fastening member at an angle such that a distal side of the fastening member may lie substantially flush against an outer surface of the bone. The fastening member may further comprise a self-locking element for engaging at least one of the protrusions and preventing said strap from moving in a distal direction when a tensile force is applied thereto.

DETAILED DESCRIPTION OF THE INVENTION

Figure 1:
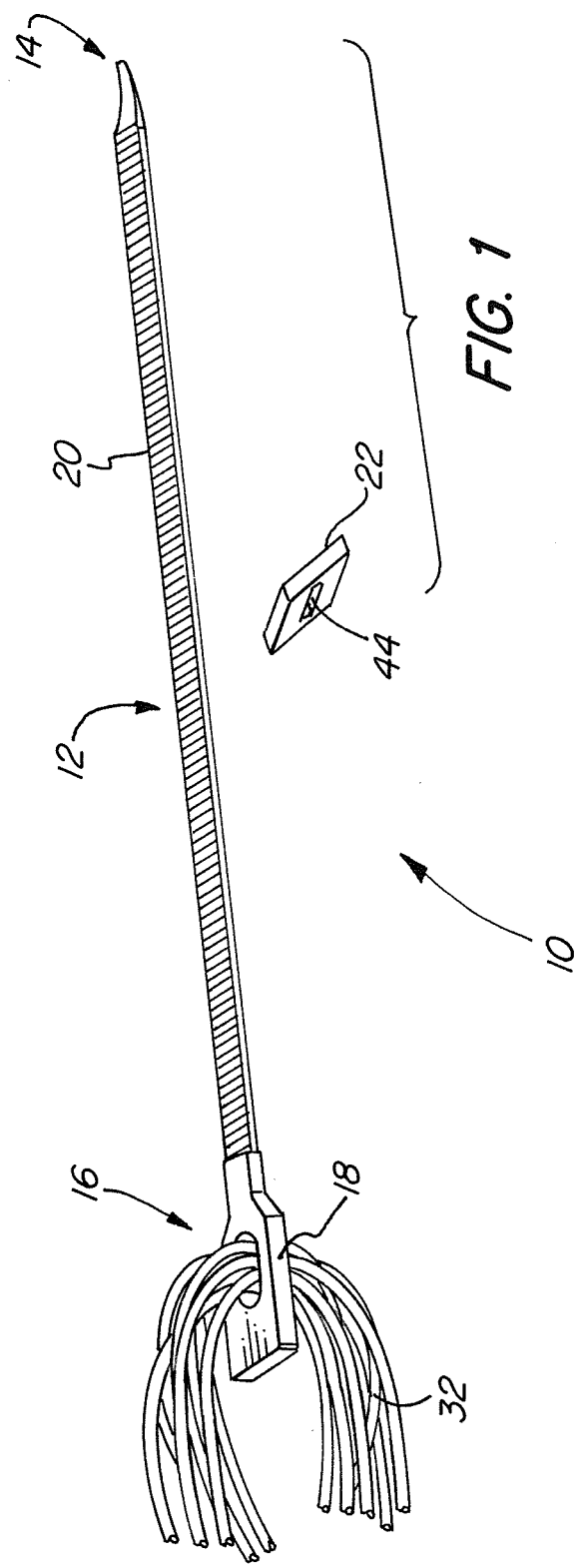
FIG. 1 is a perspective view of an embodiment of the fixation device of the present invention.

FIG. 1 depicts the fixation device 10 in accordance with the present invention, which comprises an elongate strap 12, having a proximal end 14 and a connection element 18 provided at a distal end 16 thereof, and a fastening member 22. Both the strap 12 and fastening member 22 may be made of a bioabsorbable material (such as that found in the MegaFix® interference screw), a plastic (such as PEEK) or any other suitable material.

Figure 2:
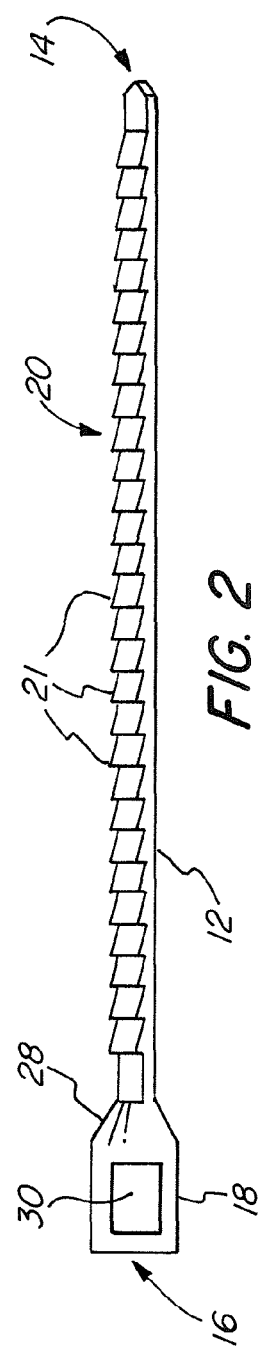
FIG. 2 is a perspective view of an embodiment of the strap of the fixation device of the present invention.
Figure 3:
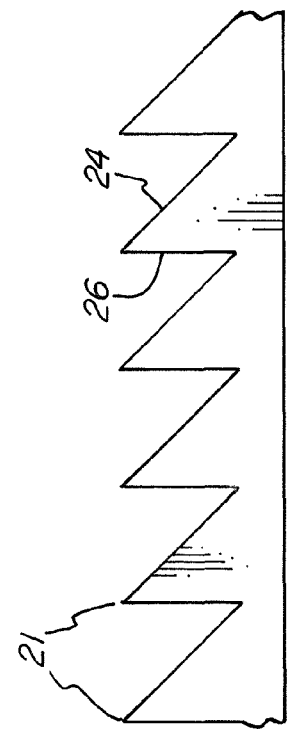
FIG. 3 is a side view of a portion of an embodiment of the strap of the fixation device of the present invention.

As shown in FIGS. 2 and 3, strap 12 further comprises a plurality of protrusions 20 along its length. In one embodiment, strap 12 is similar to a "zip-tie" or "cable-tie" known in the art, wherein the protrusions 20 are teeth 21, each having a proximal side 24 and a distal side 26, the distal side being formed at a right angle and the proximal side sloping downwards towards the proximal end 14 of the strap 12. Other configurations of the protrusions 20 are contemplated, including, but not limited to, a plurality of cones spaced along the strap. The strap 12 is also provided with a shoulder 28, the utility of which will be described below. The proximal end 14 of the strap is preferably tapered to facilitate passing it through a bone tunnel. In addition, the proximal end 14 of the strap 12 may be provided with a small hole (not shown) for connecting the strap to a guide wire or guide pin for implantation.

A replacement ACL graft may be selected, according to surgeon preference, from a portion of a patellar tendon having a bone block or plug at each end, a semitendinous graft, a fully prosthetic device, or a combination of artificial and natural material such as a ligament augmentation device (LAD) to which tissue is sutured. The terms "graft" or "transplant" are used herein to encompass all of these tissue replacement items. In order to accommodate the many types of grafts, the present invention contemplates that the connection element 18 may take a variety of forms. The particular type of graft selected will dictate how it is connected to the fixation device of the present application.

Figure 4:
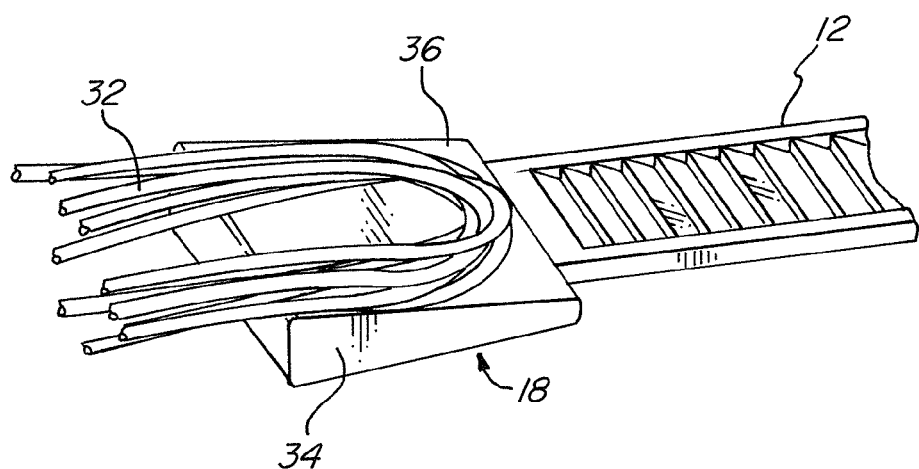
FIG. 4 is a perspective view of an embodiment of the connection element of the fixation device of the present invention.
Figure 5:
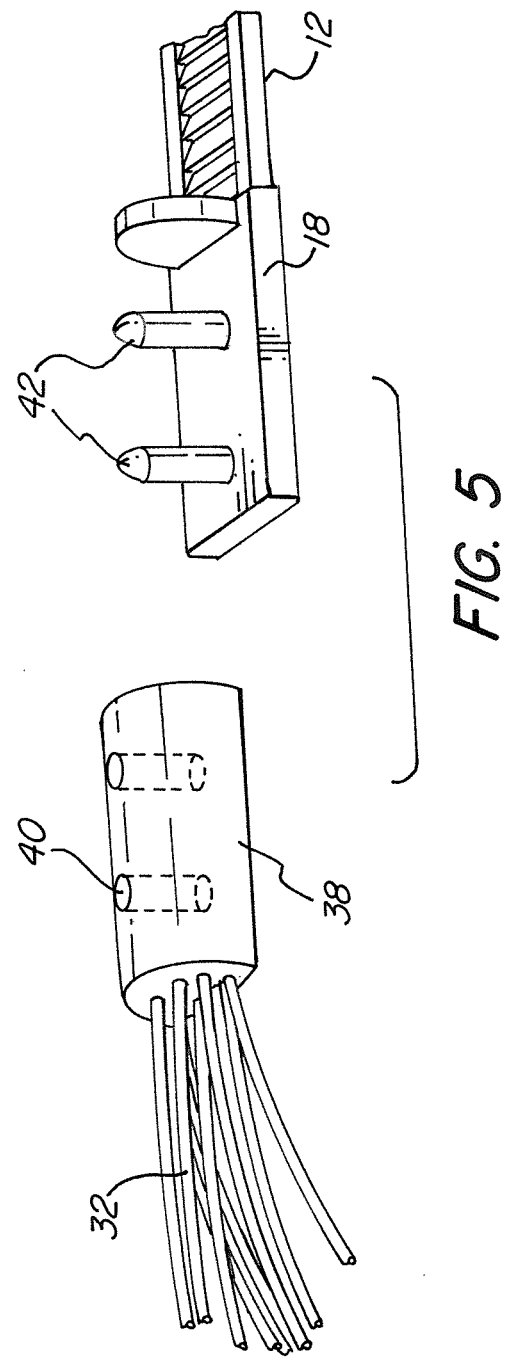
FIG. 5 is a perspective view of an embodiment of the connection element of the fixation device of the present invention.

In the embodiment shown in FIGS. 1 and 2, the connection element 18 of the strap 12 is provided as an eyelet 30 for receiving a portion a ligament transplant 32 therethrough. With this configuration, the transplant may also be connected to the eyelet 30 by means of a suture loop, rather than by being passed through the eyelet itself. In the embodiment shown in FIG. 4, the connection element 18 comprises a wedge 34. In operation, a portion of the transplant 32 would be placed on the angled surface 36 of the wedge 34 and forced against the inner surface of the bone tunnel as the strap 12 was pulled therethrough. The embodiment shown in FIG. 5 is for use with a transplant 32 having a bone block 38 with at least one hole 40 therethrough. The connection element 18 is provided with at least one prong 42 for engaging the at least one hole 40 in the bone block.

Figure 6:
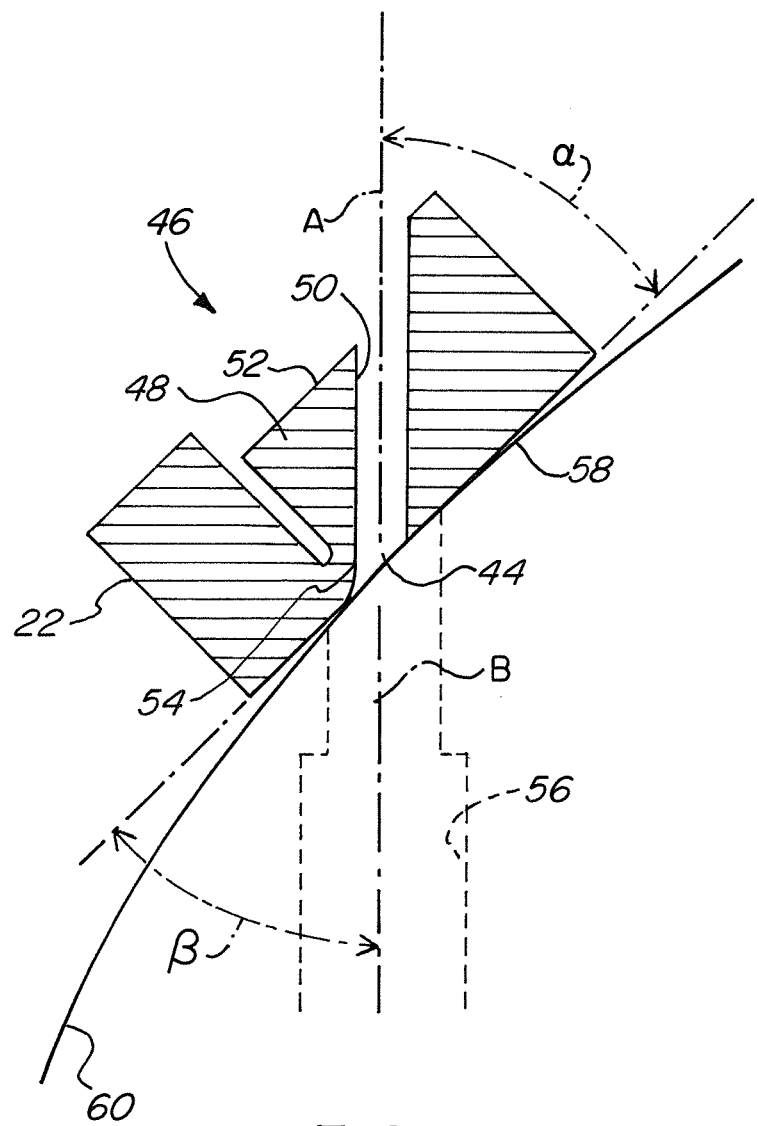
FIG. 6 is a side sectional view of an embodiment of the fastening member of the fixation device of the present invention.

Turning to FIG. 6, fastening member 20 is provided with an aperture 44 therethrough for accepting the strap 12. When fastening member 20 is oriented over a bone tunnel 56 such that its distal surface 58 lies substantially flush against an outer surface 60 of the bone, an axis A of aperture 44 is substantially parallel to the axis B of the bone tunnel. This feature is a significant advantage over the prior art, for several reasons.

It is readily apparent that in order for the fixation devices of this kind to function properly, the strap 12 must have a substantially straight trajectory from the bone tunnel through the aperture 44. If the strap 12 is forced to pass from the bone tunnel through the aperture at an angle, the strap 12 will bow, which may cause a number of undesirable effects. A bow in the strap may cause it to be pushed off to one side within the bone tunnel. This may lead to an undesirable placement of the transplant, or may cause damage to the transplant itself. This bowing effect may also cause the strap to poorly engage with the fastening member 20 or it may, over time, cause the strap to break at the point of flexion. In either case, the fixation device would be pulled back through the bone tunnel, leading to failure of the transplant.

In an ideal situation, the bone tunnel would be drilled perpendicular to the outer surface of the bone and, therefore, the aperture could be placed perpendicular within the fastening member. However, in ACL or PCL repair surgery, the femoral bone tunnel 56 is typically not provided perpendicular to the surface of the bone, but rather is provided at some angle β. Typically, the angle β of the bone tunnel is 45 degrees, in order to mimic the natural angle of incidence of the ligament.

Figure 7:
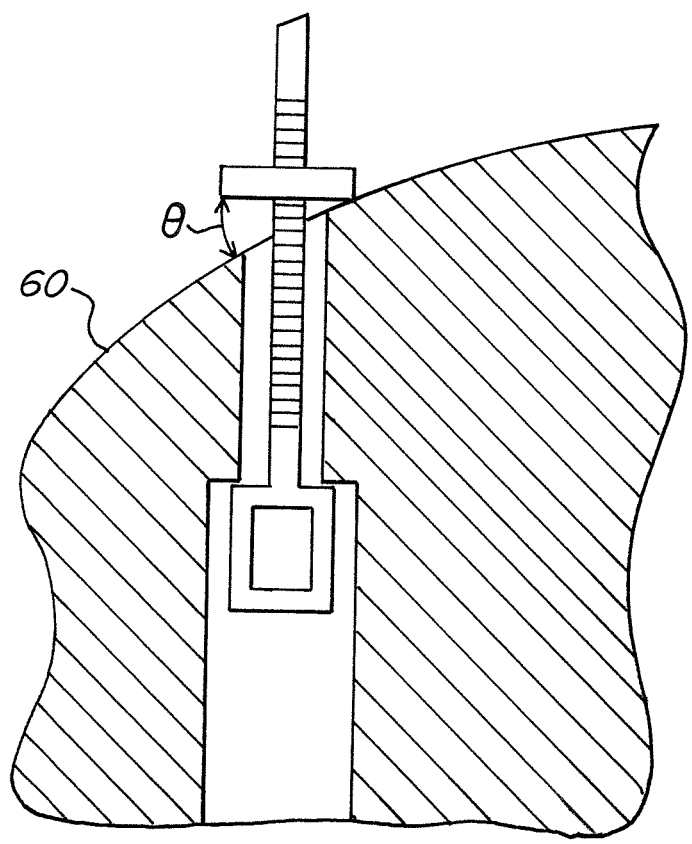
FIG. 7 is a partial side-sectional view of a fixation device of the prior art.

Thus, in the context of ACL repair, or in any other surgery where a bone tunnel is not drilled perpendicularly to the outer surface of a bone, prior art devices, such as the one of U.S. Pat. No. 6,283,996, would have significant disadvantages and would not be desirable. On the one hand, as shown in FIG. 7, if a straight path were maintained between the aperture of the fastening member and the bone tunnel, the prior art fastening member of the '996 patent would not lie flat against the outer surface of the bone, but rather a gap of some angle θ would exist between the fastening member and the bone. This configuration is highly unstable and would not provide a secure fixation of the device on the outer surface of the bone and may lead to disruption of the transplant. Moreover, this sharp angle protruding from the surface of a bone may interfere with or cause damage to other physiological structures and tissues. At the very least, this would be uncomfortable for the patient. On the other hand, if the fastening member of the '996 patent were forced against the outer surface of the bone, causing the aperture to be at some angle to the bone tunnel, this would cause the strap bow, thus causing the aforementioned associated problems.

As shown in FIG. 6, one significant advantage of the present invention over the prior art, is that when fastening member 20 is oriented over a bone tunnel 56 that is not perpendicular to the outer surface 60 of the bone, the distal surface 58 of the fastening member 20 lies substantially flush against an outer surface 60 of the bone while the axis A of the aperture 44 is maintained substantially parallel to the axis B of the bone tunnel 56. Thus, the angle α of the aperture 20 is substantially the same as the angle β of the bone tunnel 56. This orientation of the aperture 44 allows the fastening member to be fully engaged with the outer surface 60 of the bone, providing a very stable and secure connection. Moreover, the fastening member 20 is able to maintain a low profile against the outer surface of the bone, providing the least interference with surrounding tissues. This advantage is further pronounced if fastening member 20 is optionally countersunk into the outer surface of the bone.

Fastening member 20 is further provided with a self-locking element 46 for engaging at least one of the protrusions 20 and preventing the strap 12 from moving in a distal direction when a tensile force is applied thereto. In the embodiment shown in FIG. 6, the self-locking element 46 is provided as a pawl 48, having a camming surface 50, a locking surface 52 and a stem 54. The stem 54 flexibly connects the self-locking element 46 to the fastening member 20. In operation, the strap 12 is inserted into the aperture 44 and the teeth 21 of the strap 12 cooperate with the pawl 48 much like a ratchet. The sloped proximal surface 24 each tooth 21 cams over the camming surface 50 of the pawl 48 causing stem 54 to slightly flex inward until the distal side 26 of the tooth 21 engages the locking surface 52 of the pawl, automatically locking the strap and preventing it from moving back in a distal direction. This self-locking element 46 is a significant advantage over the prior art because it allows for simple and secure fixation of a transplant. Instead of having to perform complicated draw string or suturing procedures, or setting an additional locking screw or clamp member, the fixation device 10 of the present invention is secured by simply passing the fastening member 20 down the strap 12.

Figure 8:
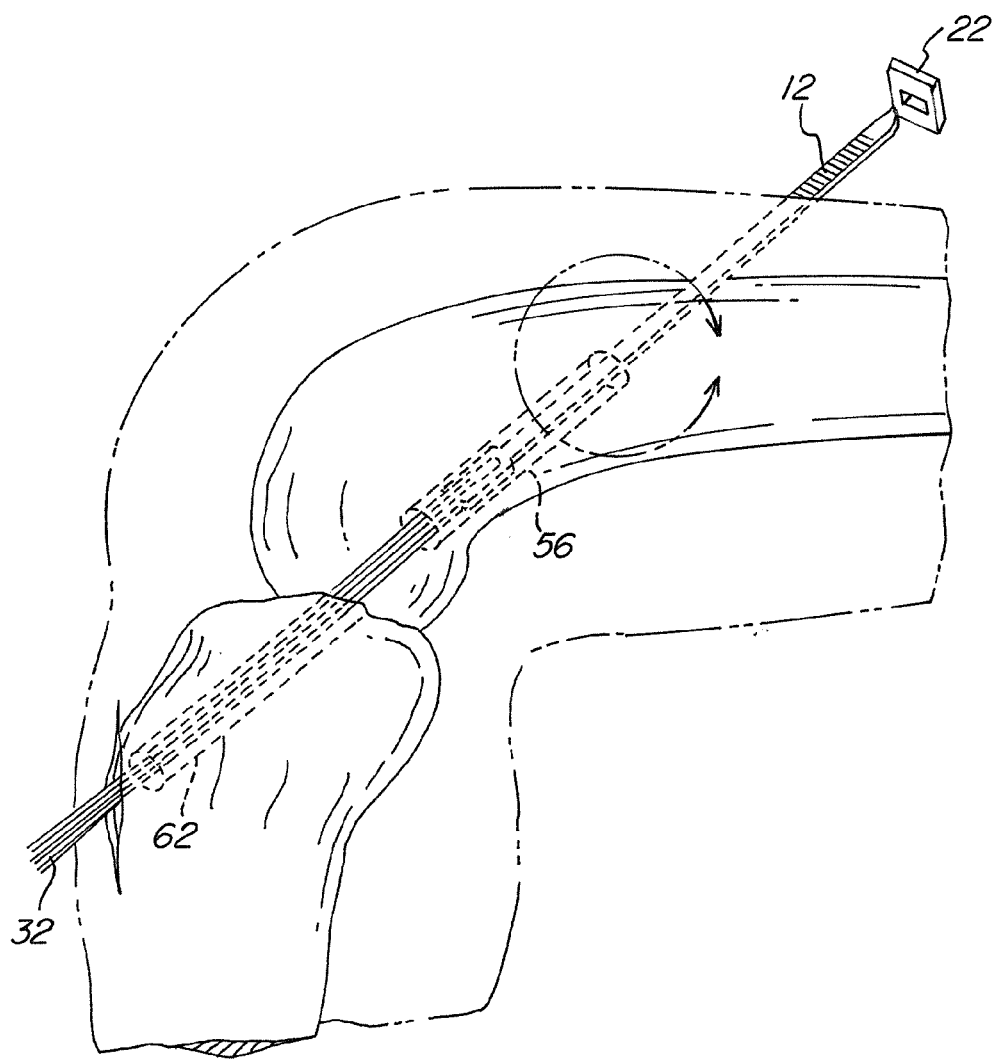
FIG. 8 is a partial cross-sectional view of a human knee showing an embodiment of the fixation device of the present invention in use.
Figure 9:
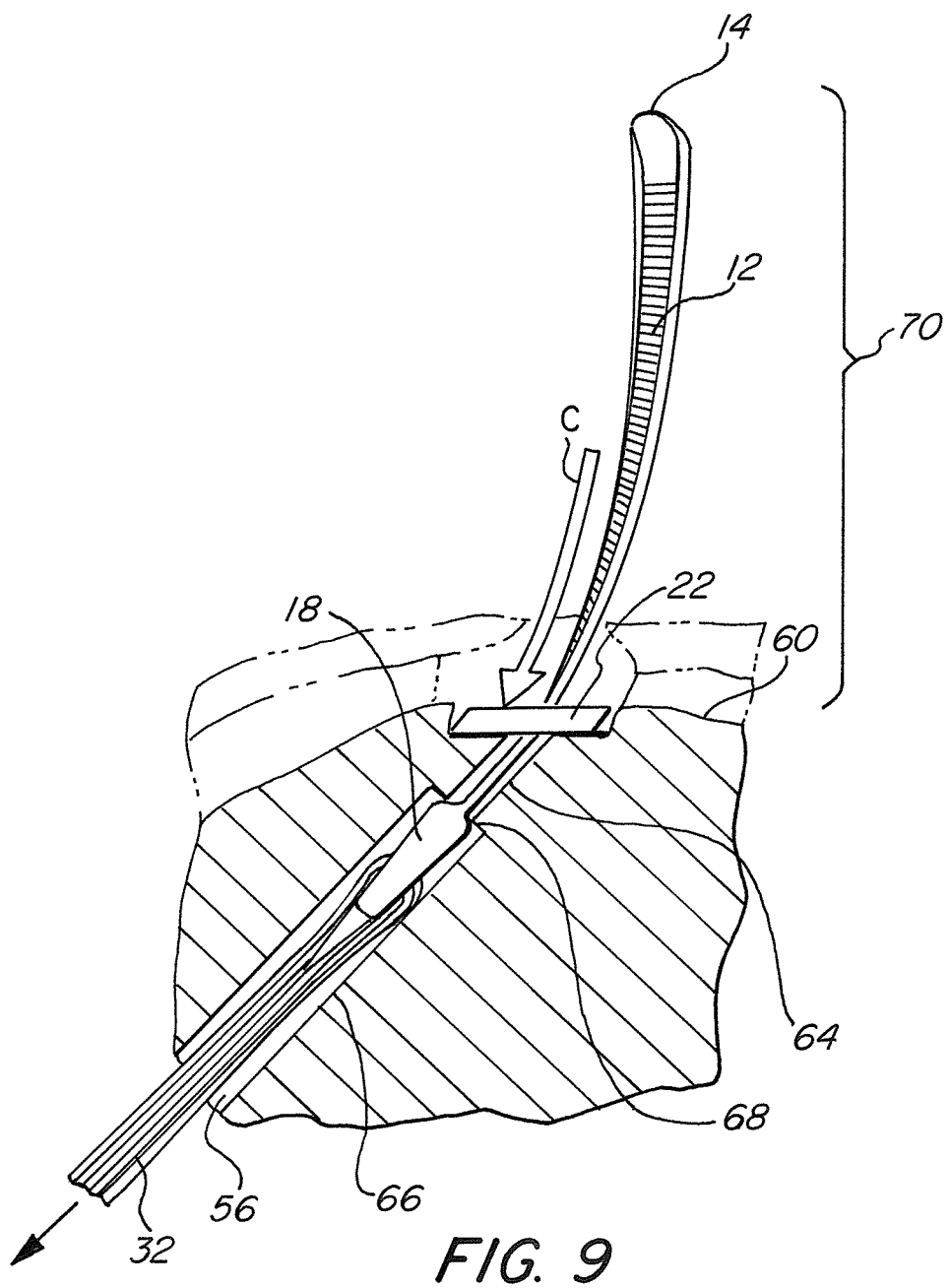
FIG. 9 is a partial cross-sectional view of a human knee showing an embodiment of the fixation device of the present invention in use.

In operation, tibial 62 and femoral 56 tunnel segments are drilled in the tibia and femur of a patient, respectively. As shown in FIG. 8, a transplant is attached to the connection member 18 of the strap 12 and the proximal end 14 of the strap 12 is attached to a guide wire or pin (not shown) which is then threaded through the tibial 62 and femoral 56 tunnel sections until the desired position and tension on the transplant is achieved. The fastening member 22 is then passed over the proximal end 14 of the strap 12 via the aperture 44 and down the length of the strap 12 in the direction of arrow C until the fastening member 22 abuts the outer surface 60 of the bone. As shown in FIG. 9, the fastening member 22 may optionally be countersunk into the bone. The excess portion 70 of the strap 12 is then clipped off near the fastening member 22 by the surgeon and removed.

While the above discussion and the Figures have been directed to a discussion of using the fixation device 10 for affixing a transplant within the femoral tunnel 56, the fixation device 10 may also be used to secure the transplant within the tibial tunnel 62. For example, the a fixation device 10 having a connection element 18 in the shape of a wedge 34 as shown in FIG. 4 may be used to secure the transplant within the tibia by means of an interference fit. Other means of fixating the transplant within the tibial tunnel 62 through use of the fixation device 10 of the present invention are contemplated.

As further shown in FIG. 9, the femoral tunnel 56 may be provided with a first 64 section proximal of a second section 66, the sections being coaxial and the first section 64 having a smaller radius than the second section 66. The intersection of these two sections defines a notch 68 within the bone tunnel 56. In this embodiment, the strap 12 will be passed through the bone tunnel 56 until the shoulder 28 of the strap 12 rests on the notch 68. This not only provides guidance for the surgeon for properly placing the fixation device 10, but also provides resistance from the transplant being pulled out in the proximal direction.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A fixation device for securing a transplant in a bone tunnel, comprising:
a strap having a plurality of protrusions disposed along its length;
a fastening member having an aperture therein for passing the strap; and
a connection element disposed at a distal end of said strap for engaging a transplant;
said connection element further comprising a shoulder adapted to engage a notch within the bone tunnel, said shoulder having a width that is greater than a diameter of a first tunnel section in the bone and that is smaller than a diameter of a second tunnel section in a bone disposed distally of said first tunnel section;
said fastening member further comprising a distal side, a longitudinal axis of said aperture being substantially parallel to a longitudinal axis of said bone tunnel when said fastening member distal side lies substantially flush against an outer surface of the bone;
said fastening member further comprising a self-locking element having a camming surface adjacent to a locking surface positioned to engage at least one of said plurality of protrusions and a stem, said camming surface defining a portion of said aperture and said locking surface being parallel to the distal side of said fastening member, wherein said camming surface is positioned at a 45 degree angle with respect to the distal side of said fastening member, said stem flexibly connecting said self-locking element to said fastening member; wherein upon insertion of said strap within said aperture, said plurality of protrusions cause said stem to flex slightly inward until said plurality of protrusions engage said locking surface.

2. The fixation device of claim 1 wherein the longitudinal axis of said aperture is coaxial with the longitudinal axis of said bone tunnel.

3. The fixation device of claim 1 wherein said aperture traverses said fastening member at a 45 degree angle with respect to a longitudinal axis of said fastening member.

4. The fixation device of claim 1 wherein said plurality of protrusions comprise a plurality of teeth.

5. The fixation device of claim 4 wherein said self-locking element comprises a pawl shaped to engage at least one of said plurality of teeth.

6. The fixation device of claim 4 wherein said teeth comprise a proximal side and a distal side, the proximal side of each of said teeth sloping downwards towards a proximal end of the strap.

7. The fixation device of claim 1 wherein said connection element comprises an eyelet for receiving a portion of said transplant therethrough.

8. The fixation device of claim 1 wherein said connection element comprises a wedge for pressing a transplant against an inner surface of said bone tunnel.

9. The fixation device of claim 1 wherein said connection element comprises at least one prong for engaging a hole in a bone block of a transplant.

10. A fixation device for securing a transplant in a bone tunnel, comprising:
    a strap having a plurality of protrusions disposed along its length;
    a fastening member having an aperture therein for passing the strap; and
    a connection element disposed at a distal end of said strap for engaging a transplant;
    said aperture traversing said fastening member at a 45 degree angle with respect to a longitudinal axis of said fastening member;
    said fastening member further comprising a distal side, a longitudinal axis of said aperture being substantially parallel to a longitudinal axis of said bone tunnel when said fastening member distal side lies substantially flush against an outer surface of the bone;
    said fastening member further comprising a self-locking element having a camming surface adjacent to a locking surface positioned to engage at least one of said plurality of protrusions and a stem, said camming surface defining a portion of said aperture and said locking surface being parallel to the distal side of said fastening member, said stem flexibly connecting said self-locking element to said fastening member;
    wherein upon insertion of said strap within said aperture, said plurality of protrusions cause said stem to flex slightly inward until said plurality of protrusions engage said locking surface.

11. The fixation device of claim 10 wherein said camming surface is positioned at a 45-degree angle with respect to the distal side of said fastening member.

* * * * *